United States Patent
Price

(10) Patent No.: US 7,537,579 B2
(45) Date of Patent: May 26, 2009

(54) SAFETY INTERLOCK SYSTEM FOR AN ENTERAL FEEDING PUMP

(75) Inventor: Jeffrey Price, Wildwood, MO (US)

(73) Assignee: Covidien AG (CH)

( * ) Notice: Subject to any disclaimer, the term of this patent is extended or adjusted under 35 U.S.C. 154(b) by 0 days.

(21) Appl. No.: 11/219,974

(22) Filed: Sep. 6, 2005

(65) Prior Publication Data

US 2006/0004327 A1    Jan. 5, 2006

Related U.S. Application Data

(63) Continuation-in-part of application No. PCT/US03/10713, filed on Apr. 7, 2003.

(60) Provisional application No. 60/413,710, filed on Sep. 26, 2002.

(51) Int. Cl.
*A61M 31/00* (2006.01)

(52) U.S. Cl. .................................. 604/65; 604/246

(58) Field of Classification Search ............ 604/65–67, 604/151–154, 249, 131, 246, 250; 324/654
See application file for complete search history.

(56) References Cited

U.S. PATENT DOCUMENTS

| | | | |
|---|---|---|---|
| 4,002,996 A * | 1/1977 | Klebanoff et al. ............... 331/65 |
| 4,551,134 A | 11/1985 | Slavik et al. |
| 4,758,228 A | 7/1988 | Williams |
| 4,882,575 A | 11/1989 | Kawahara et al. |
| 4,884,013 A * | 11/1989 | Jackson et al. ............... 318/481 |
| 4,898,579 A | 2/1990 | Groshong et al. |
| 4,913,703 A | 4/1990 | Pasqualucci et al. |
| 5,147,312 A | 9/1992 | Walker et al. |
| 5,181,842 A | 1/1993 | Sunderland et al. |
| 5,201,711 A | 4/1993 | Pasqualucci et al. |
| 5,250,027 A | 10/1993 | Lewis et al. |
| 5,330,431 A | 7/1994 | Herskowitz |
| 5,374,251 A | 12/1994 | Smith |
| 5,431,627 A | 7/1995 | Pastrone et al. |
| 5,462,525 A * | 10/1995 | Srisathapat et al. ............ 604/67 |
| 5,567,120 A | 10/1996 | Hungerford et al. |
| 5,601,420 A | 2/1997 | Warner et al. |
| 5,634,907 A | 6/1997 | Rani et al. |
| 5,743,878 A | 4/1998 | Ross et al. |
| 5,781,005 A * | 7/1998 | Vig et al. ................... 324/207.2 |
| 5,899,665 A | 5/1999 | Makino et al. |
| 6,017,326 A * | 1/2000 | Pasqualucci et al. ......... 604/153 |

(Continued)

FOREIGN PATENT DOCUMENTS

WO    WO 2004028595 A1 *    4/2004

*Primary Examiner*—Nicholas D Lucchesi
*Assistant Examiner*—Theodore J Stigell
(74) *Attorney, Agent, or Firm*—Edward S. Jarmolowicz, Esq.

(57) ABSTRACT

A safety interlock system for a flow control apparatus is disclosed that permits operation when a magnet-less administration feeding set is properly mounted to recess formed along the housing of the flow control apparatus. The administration feeding set comprises flexible patient tubing having a support member at one end and a mounting member including a magnetically-susceptible metallic component at the other end thereof. A sensing arrangement is provided by the flow control apparatus for sensing the proper engagement of the metallic component to the recess of the flow control apparatus. A control means permits operation of the flow control apparatus when the metallic member is properly engaged to recess, while terminating operation when the metallic member is improperly engaged to recess.

6 Claims, 5 Drawing Sheets

U.S. PATENT DOCUMENTS 6,325,422 B1      12/2001  Verkaart et al.
6,724,198 B2 *    4/2004   Hohl .......................... 324/654
6,907,788 B2      6/2005   Malmstrom et al.

* cited by examiner

SAFETY INTERLOCK SYSTEM FOR AN ENTERAL FEEDING PUMP

RELATED APPLICATIONS

This application is a continuation in part of 371 National Stage Application for International Application PCT/US03/10713, filed Apr. 7, 2003, which claims priority from U.S. Provisional Patent Application No. 60/413,710, filed Sep. 26, 2002.

BACKGROUND OF THE INVENTION

1. Field of the Invention

The present invention relates to a safety interlock system, and more particularly to a safety interlock system for a flow control apparatus. More specifically, the present invention relates to a safety interlock system using a magnet-less administration feeding set with an enteral feeding pump.

2. Prior Art

Enteral feeding systems are frequently used for patients who are unable to take nutrition alone and require some type of feeding system to provide nutrition through a gastrointestinal tract of a patient, such as the stomach. Typically, an enteral feeding system comprises a disposable administration feeding set in conjunction with a flow control apparatus, such as a pump, for supplying fluid to a patient at a controlled delivery rate. The administration feeding set of the prior art includes an inlet tube in communication with a source of fluid at one end and a drip chamber which is arranged to be mounted along a first recess on the pump at the other end, a mounting member for mounting the administration feeding set to a second recess on the pump, and a pump tube which connects the drip chamber to the mounting member while engaging a motor driven rotor on the pump.

In many enteral feeding systems the engagement of the pump tube to the rotor controls the flow of fluid to the patient according to the speed of the rotor. In the event the administration feeding set is not properly mounted to the pump, an excess flow of fluid through the feeding set can occur under force of gravity which is highly undesirable. Improper mounting of the drip chamber is unlikely because of the mechanical configuration of that component and its corresponding recesses on the pump. However, improper placement of the mounting member, e.g. below, above or outside of the respective recess on the pump is more likely if the administration feeding set is improperly installed on the pump by an inexperienced operator who has not yet received proper instruction in the operation of the enteral feeding system. Instances of such improper installation of the administration feeding set have been reported.

U.S. Pat. Nos. 4,913,703; 5,201,711; and 6,017,326 to Pasqualucci et al. disclose a safety interlock system for a flow control apparatus provided with a magnetic field source in the region of its mounting to an administration feeding set having a magnetic source, such as a magnet, incorporated into the mounting member. The flow control apparatus includes a magnetic field sensitive switching component which detects the proper placement of administration feeding set in the recess of the flow control apparatus and prevents operation of the flow control apparatus unless the mounting member of the administration feeding set is in a properly engaged position to the pump. Although the safety interlock system of Pasqualucci et al. provides an excellent means of ensuring proper engagement of the administration feeding set on the flow control apparatus, the magnet used to provide the magnetic source on the disposable administration feeding set makes it relatively expensive to manufacture.

Therefore, there appears a need in the art for a safety interlock system that is inexpensive to manufacture. There is a further need in the art for a safety interlock system that does not require an administration feeding set having a magnet in order to ensure proper placement of the feeding set on the flow control apparatus.

OBJECTS AND SUMMARY OF THE INVENTION

Accordingly, the primary object of the present invention is to provide a safety interlock system for an enteral feeding system that ensures the proper placement of the administration feeding set on a flow control apparatus.

Another object of the present invention is to provide an administration feeding set for a safety interlock system having no magnetic source, such as a magnet.

A further object of the present invention is to provide an administration feeding set for a safety interlock system that is inexpensive to manufacture.

Another further object of the present invention is to provide a safety interlock system having a sensor arrangement inside the flow control apparatus for detection of a magnetically-susceptible metallic component on the administration feeding set.

Yet a further object of the present invention is to provide an administration feeding set for a safety interlock system having a sensor arrangement inside the flow control apparatus that senses a variation in the magnetic field when the feeding set is properly installed.

These and other objects of the present invention are realized in the preferred embodiment of the present invention, described by way of example and not by way of limitation, which provides for a magnet-less administration feeding set for a safety interlock system used in a flow control apparatus.

In brief summary, the present invention overcomes and substantially alleviates the deficiencies in the prior art by providing a safety interlock system for an enteral feeding system comprising an administration feeding set adapted for operative engagement with a flow control apparatus for delivery of fluid at a controlled rate to a patient.

According to one aspect of the present invention there is provided a method for preventing improper system operation which comprises the steps of providing a sensor arrangement inside the flow control apparatus which is operatively associated with a switching component that places the flow control apparatus in a first electrical state when the administration feeding set is properly mounted to the flow control apparatus and a second electrical state when the administration feeding set is not properly mounted to the flow control apparatus. In operation, the flow control apparatus is enabled in response to the first electrical state and disabled in response to the second electrical state. The second electrical state will prevent the flow control apparatus from operating while causing an alarm to be activated when operation of the flow control apparatus is attempted.

In accordance with another aspect of the present invention there is provided a flow control apparatus which is arranged to receive a corresponding administration feeding set. The switching component is responsive to the proper mounting of the administration feeding set and is provided with a control means responsive to the switching component for permitting operation of the flow control apparatus only when the switching component detects proper mounting of the administration feeding set. Preferably, the switching component is operatively associated with a sensor arrangement comprising a Hall-effect sensor and magnet reconfigured to be back-biased to enable detection of a magnetically-susceptible metallic component on the administration feeding set by the switching component when the feeding set is properly mounted to the flow control apparatus.

In accordance with another aspect of the present invention there is provided a disposable administration feeding set adapted to be operatively connected to a flow control apparatus for controlled delivery of fluid to a patient. The flow control apparatus includes a switching component for interrupting the operation thereof when the administration feeding set is improperly engaged to the flow control apparatus, wherein the administration feeding set includes a magnetically-susceptible metallic component for detection by the sensor arrangement which activates the switching component upon improper operative engagement of the tubing and prevents operation of the flow control apparatus.

In accordance with another aspect of the present invention there is also provided a disposable administration feeding set including flexible tubing adapted to be operatively connected to the flow control apparatus, wherein the administration feeding set includes a magnetically-susceptible metallic component for detection by the sensor arrangement which activates the switching component to permit flow control apparatus operation only upon proper operative engagement of the feeding set thereto.

Additional objects, advantages and novel features of the invention will be set forth in the description which follows, and will become apparent to those skilled in the art upon examination of the following more detailed description and drawings in which like elements of the invention are similarly numbered throughout.

DETAILED DESCRIPTION OF THE INVENTION

Figure 1:
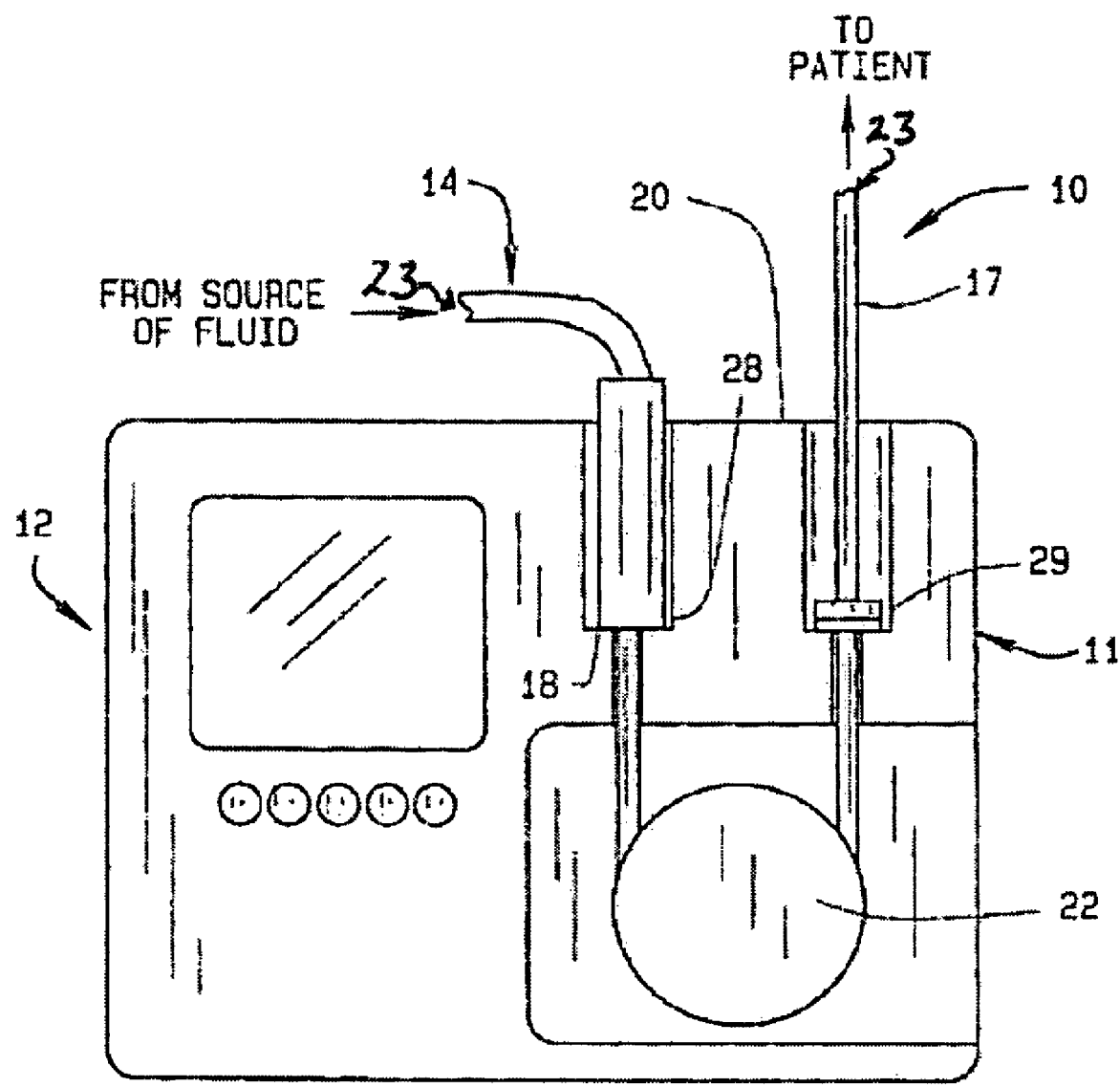
FIG. 1 is a perspective view of the enteral feeding system according to the present invention.
Figure 6:
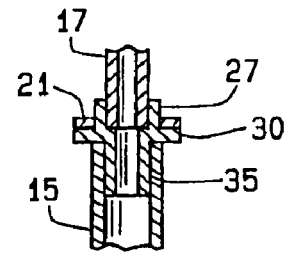
FIG. 6 is a cross-sectional view of the mounting member taken along lines 5-5 of FIG. 4 according to the present invention.
Figure 8:
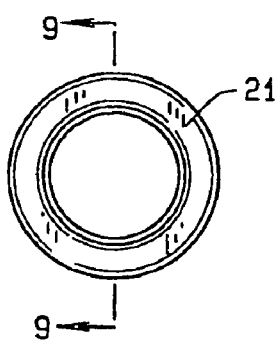
FIG. 8 is plan view of a magnetically-susceptible metallic component according to the present invention.
Figure 9:
FIG. 9 is a cross-sectional view of the magnetically-susceptible metallic component taken along lines 8-8 of FIG. 7 according to the present invention.

Referring to the drawings, the preferred embodiment of the safety interlock system according to the present invention is illustrated and generally indicated as 11 in FIG. 1. Safety interlock system 11 is preferably used with a flow control apparatus 12, such as a peristaltic pump or other suitable infusion device, of an enteral feeding system 10 for providing fluid to a patient's gastrointestinal tract (not shown) at a controlled rate of delivery. An administration feeding set 14 is operatively engaged with a flow control apparatus 12 for transporting fluid through an inlet tube 16 connected to a source of fluid (not shown) at one end and a pump tube 15 at the opposite end (FIGS. 6 an 7). Administration feeding set 14 further includes a support member 18 attached between the inlet tube 16 and the pump tube 15 for direct engagement of the feeding set 14 to the flow control apparatus 12 as shall be explained in greater detail below. In an alternative embodiment of administration feeding set 14, a drip chamber (not shown) may be substituted for the support member 18 in order to control the flow of fluid through the feeding set 14.

Figure 2:
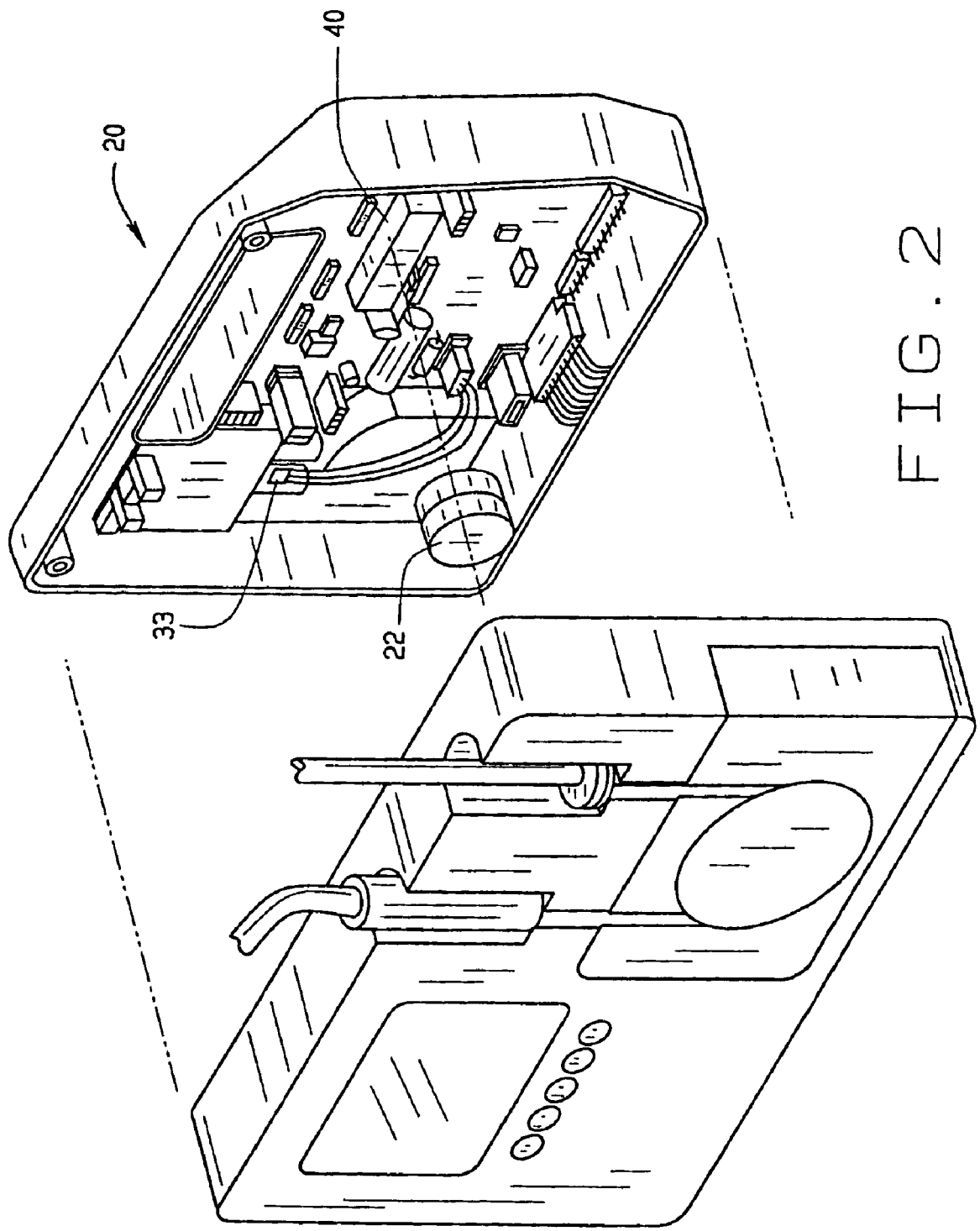
FIG. 2 is a perspective view of the enteral feeding system illustrating the interior of the flow control apparatus according to the present invention.

Referring to FIGS. 1 2 and 3, flow control apparatus 12 comprises a rotor 22 driven by a motor (not shown) that rotates rotor 22 at a predetermined speed at specific time intervals between cycles of rotor 22 to control the rate of delivery of fluid through administration feeding set 14. In addition, delivery of fluid may also be controlled by varying the angle of rotation of rotor 22 on each cycle. A housing 20 encloses the motor and forms recesses 28 and 29 for properly mounting of administration feeding set 14. As shown, pump tube 15 is attached to support member 18 at its inlet end 44 and to a mounting member 30 at its outlet end 46. When properly engaging the administration feeding set 14 to flow control apparatus 12, support member 18 is seated in recess 28, pump tube 15 is engaged around rotor 22, and mounting member 30 is properly mounted in recess 29.

Figure 5:
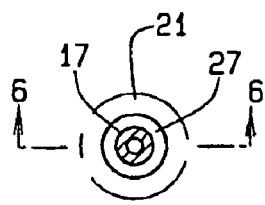
FIG. 5 is a top view of a mounting member according to the present invention.
Figure 7:
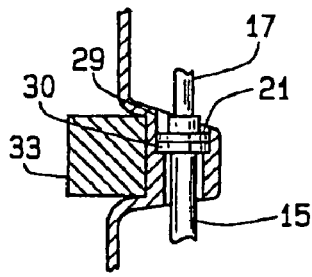
FIG. 7 is a cross-sectional view of a safety interlock system taken along lines 6-6 of FIG. 1 according to the present invention.

Referring to FIGS. 1, 5 and 6, mounting member 30 is attached to the outlet end of pump tube 15 by an engaging member 35 on the bottom side of member 30 and a tube receiving member 27 at the top side thereof. As further shown, a circular shaped magnetically-susceptible metallic component 21 is disposed within mounting member 30 which surrounds pump tube 15. An outlet tube 17 is attached to the tube receiving member 27 for allowing fluid flow to the patient from pump tube 15.

In accordance with one aspect of the present invention, safety interlock system 11 provides a means for assuring the proper placement of administration feeding set 14 on flow control apparatus 12, and in particular with the proper placement of the pump tube 15 around the rotor 22 to form a peristaltic pump which provides accurate and controlled delivery rate of fluid through feeding set 14.

Figure 3A:
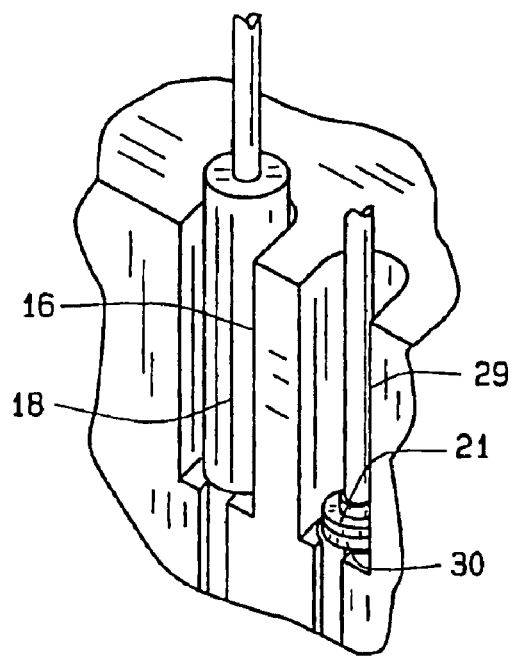
FIG. 3A is a perspective view illustrating the internal arrangement of the safety interlock system according to the present invention.

As illustrated in FIGS. 1 and 3A, support member 18 is received in recess 28 and mounting member 30 is received in recess 29. When properly mounted, pump tube 15, which is typically made from silicone tubing, is tightly stretched around rotor 22 so that the points of the rotor 22 contact on pump tube 15 and progressively close the conduit 23 thereof during operation. Referring to FIG. 3A, there is shown the proper placement of the administration feeding set 14 on flow control apparatus 12 such that the support member 18 is properly seated in recess 28 and mounting member 30 is mounted into recess 29.

Figure 3B:
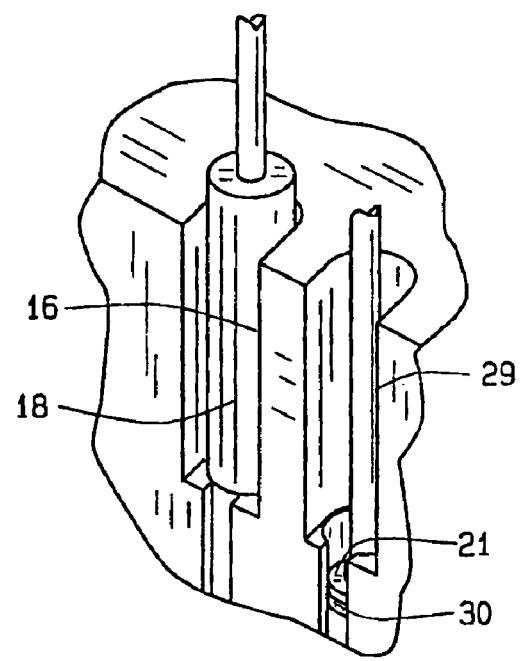
FIGS. 3B-3D are perspective views illustrating the improper placement of the safety interlock system according to the present invention.
Figure 3C:
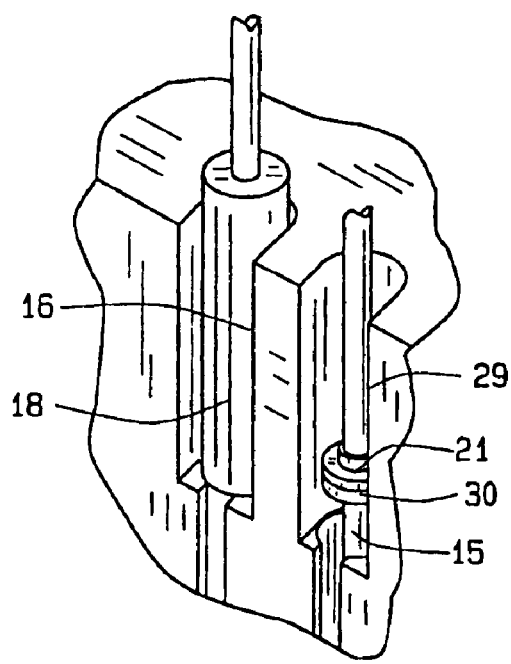
Figure 3D:
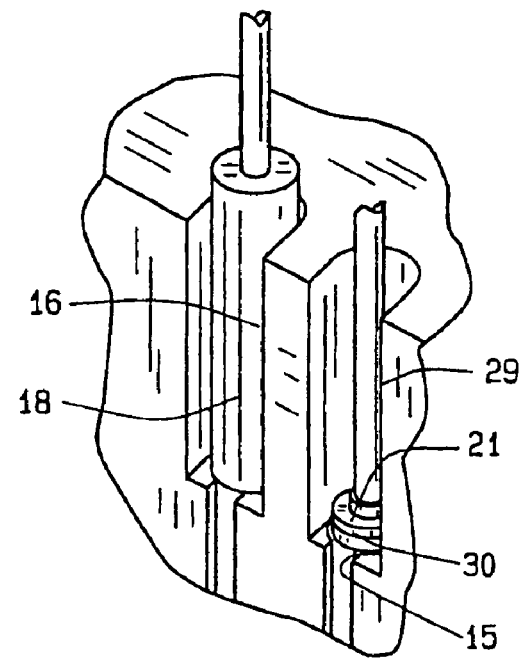

A person of ordinary skill in the art will appreciate that in some cases the mounting member 30 of safety interlock system 11 may be improperly installed by inexperienced personnel so that the mounting member 30 is seated below recess 29 as shown in FIG. 3B. This particular arrangement can be hazardous to a patient because of excess and uncontrolled flow of fluid through the administration feeding set under force of gravity, whereby fluid is delivered at a higher rate than properly specified for the patient. Another improper mounting of the administration feeding set is illustrated in FIG. 3C, wherein mounting member 30 is caught on the lip of recess 29 and not properly seated therein. Finally, another improper mounting is shown in FIG. 3D wherein mounting member 30 is not placed completely back into recess 29, but seats on the outer edge thereof. On the other hand, experience has shown that improper placement of drip chamber 18 itself is unlikely since it must be seated in both recesses 28 and 28 in order to be properly engaged.

Figure 4:
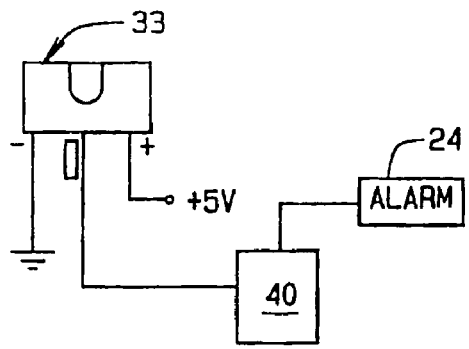
FIG. 4 is a schematic diagram illustrating the electrical connection of a switching component according to the present invention.
Figure 4A:
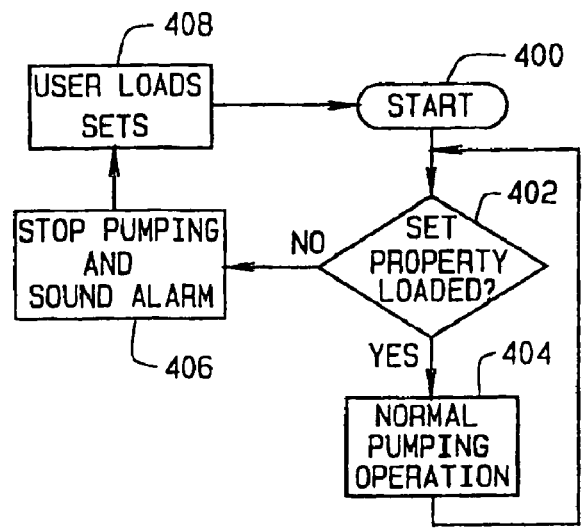
FIG. 4a is a flow chart illustrating the flow logic of the microcontroller according to the present invention.
Figure 10:
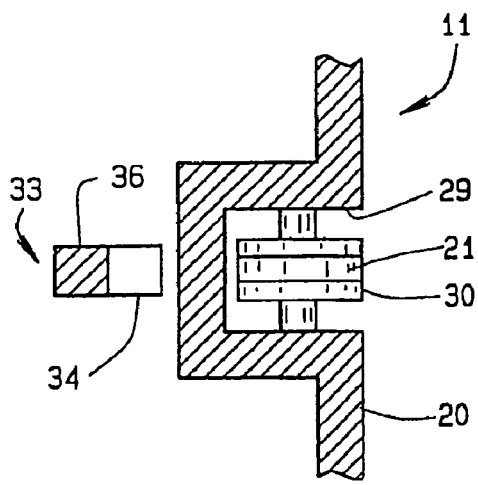
FIG. 10 is a simplified block diagram showing a preferred embodiment of the safety interlock system using a back biased sensor arrangement according to the present invention.
Figure 10A:
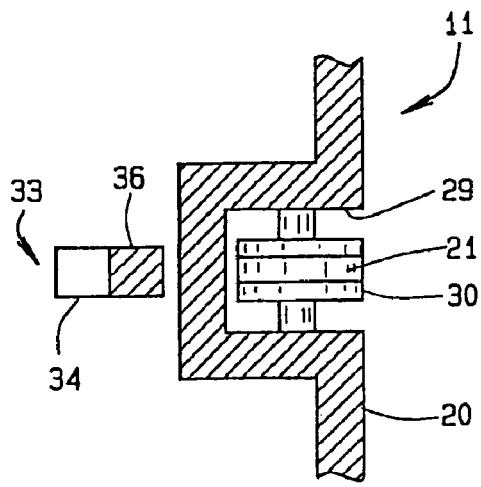
FIG. 10A is a simplified block diagram of an alternative arrangement shown in FIG. 10 of the safety interlock system according to the present invention.

In accordance with a preferred embodiment (FIGS. 2, 7 and 10) of the present invention, a sensor arrangement 33 preferably comprising a back-biased sensor 34 is provided inside flow control apparatus 12 for detecting the proper placement of mounting member 30 in recess 29. Referring to FIGS. 5-9, the metallic component 21, preferably a ferrous alloy, is used to detect the proper placement of mounting member 30 in recess 29 which is a toroidal shaped component added to mounting member 30 that surrounds the fluid passage of pump tube 15. Preferably, back-biased sensor 34 is provided within housing 20 and arranged to detect the presence of the metallic component 21 when mounting member 30 is properly seated within recess 29. FIGS. 1 and 2 show the internal arrangement of housing 20 indicating the proper placement of metallic component 21 against the inner wall adjacent recess 29. Back-biased sensor 34 comprises a sensor arrangement 33 including a biasing magnet 36 operatively associated with a Hall-Effect or magneto-resistive sensor 34, as illustrated in FIG. 10. In configuration, sensor 34 is interposed between recess 29 and biasing magnet 36 such that the magnetic flux between the magnet 36 and sensor 34 is changed by the presence of the metallic component 21 when the mounting member 30 is properly seated in recess 29. This change in magnetic flux caused by the metallic component 21 being properly received within recess 29 is sensed by sensor arrangement 33 and a signal is communicated to a microcontroller 40 (FIG. 4), or other control means, which will halt the operation of flow control apparatus 12 and an alarm is sounded as shown in FIG. 4. Therefore, when the mounting member 30 is disengaged from the recess 29, improperly seated therein, or the metallic component 21 is displaced during operation, the metallic component 21 is not sensed by the sensor arrangement 33 and the microcontroller 40 terminates operation of the flow control apparatus 12 and sound an alarm. This operation is illustrated in FIG. 4A wherein after the operation of flow control apparatus 12 is started at step 400, the microcontroller 40 determines whether the administration feeding set 14, and more particularly the mounting member 30, is properly seated in recess 29. If the microcontroller 40 determines that the administration feeding set 14 is properly mounted, then normal operation of the flow control apparatus 12 is permitted at step 404. However, if the microcontroller 40 determines that the administration feeding set 14 is improperly mounted to the recess 29, then operation of the flow control apparatus 12 is terminated and an alarm is sounded at step 406. After operation is terminated, the user must then re-load the administration feeding set 14 to the flow control apparatus at step 408 which allows the microcontroller 40 to start operation at step 400.

Figure 11:
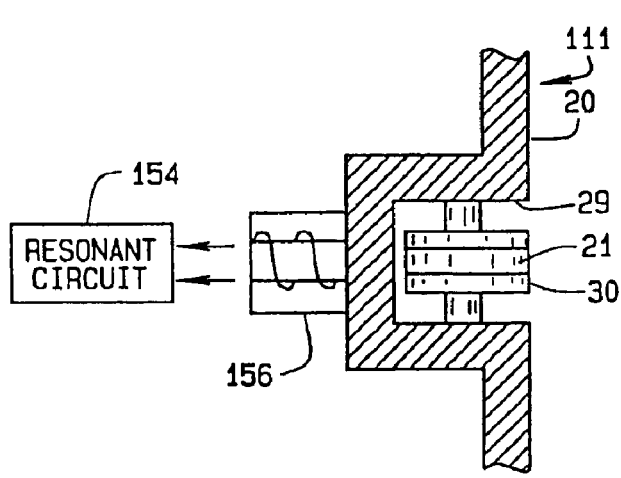
FIG. 11 is a simplified block diagram showing an alternative embodiment of the safety interlock system using a resonant coil arrangement according to the present invention.
Figure 11A:
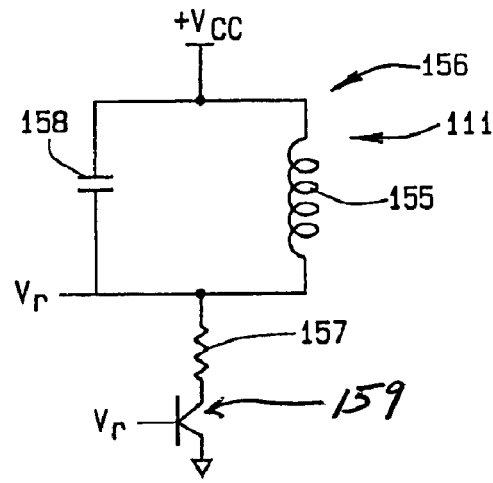
FIG. 11A is a schematic diagram showing of the alternative embodiment shown in FIG. 11 of the safety interlock system according to the present invention.

In accordance with another aspect of the present invention an alternative embodiment 111 of safety interlock system is contemplated. As shown in FIGS. 11 and 11A, safety interlock system 111 comprises a resonant circuit 154 with a coil arrangement 156 which collectively act as a resonant coil arrangement or tank circuit. In configuration, coil arrangement 156 is disposed along the inner housing 20 of flow control apparatus 12 such that arrangement 156 is directly interposed between the resonant circuit 154 and metallic component 21 when component 21 is properly received within recess 29. As shown in FIG. 11A, resonant circuit 154 comprises a capacitor 158 in parallel with an inductive coil 155 which are both connected to a transistor 159 through a resistor 157 that produces a resonant frequency with coil arrangement 156 of:

$$\tfrac{1}{2}\Pi\sqrt{LC}$$

where L is the inductance of inductive coil 155 and C is the capacitance of capacitor 158.

In operation, when metallic component 21 is properly received within recess 29, the presence of component 21 changes the resonant frequency produced by resonant circuit 154. The change in inductance produced in inductive coil 155 in the presence of metallic component 21 changes the resonant frequency to: where L1 is the inductance of inductive coil 155 in the presence of metallic $$\tfrac{1}{2}\Pi\sqrt{L_1C}$$

component 21. This change in resonant frequency is detected at Vr, the voltage response of the resonant circuit 154, which is then communicated to microcontroller 40.

Figure 12:
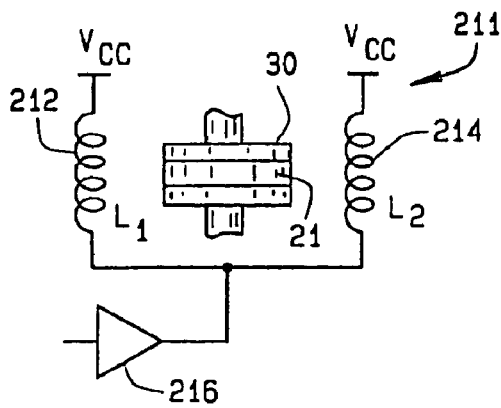
FIG. 12 is a schematic diagram showing another alternative embodiment of the safety interlock system using a balanced coil arrangement according to the present invention.

In accordance with another aspect of the present invention an alternative embodiment 211 of safety interlock system is contemplated. Referring to FIG. 12, safety interlock system 211 comprises a first inductive coil 212 in parallel with a second inductive coil 214 which are both driven by a driver circuit 216 connected to a power source (not shown) which collectively act as a balanced coil arrangement. First and second inductive coils 212 and 214 are wound in opposing directions such that the inductive coils 212 and 214 produce a resonant frequency of: where L1 and L2 are the inductance of the first and second inductive coils $$\tfrac{1}{2}\Pi\sqrt{(\sqrt{L_1L_2})}$$

212 and 214, respectively. The above arrangement assumes that the first and second inductive coils 212 and 214 are sufficiently spaced apart as to have negligible mutual interactions.

In configuration, first and second inductive coils 212 and 214 are arranged such that metallic component 21 is placed directly between inductive coils 212 and 214 when properly received within recess 29. Such placement of the metallic component 21 changes the resonant frequency produced between first and second inductive coils 212 and 214 by altering the coupling between the first and second inductive coils 212 and 214 by reducing the sum total of L1 and L2 which can then be detected at voltage Vcc and communicated to mocrocontroller 40.

Figure 13:
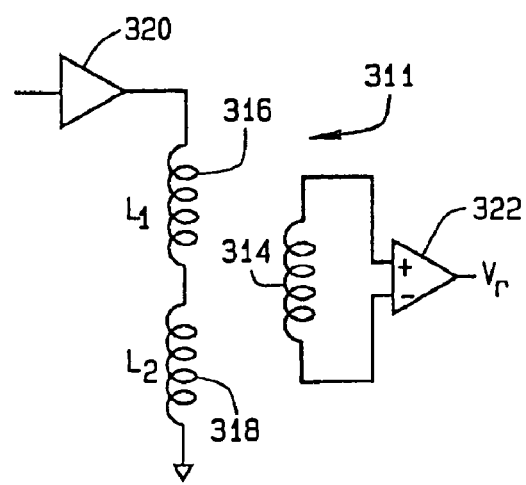
FIG. 13 is a schematic diagram showing another alternative embodiment of the safety interlock system using a differential active coil arrangement according to the present invention.

In accordance with another aspect of the present invention an alternative embodiment 311 of safety interlock system is contemplated. As illustrated in FIG. 13, safety interlock system 311 comprises a driver circuit 320 which drives a first driver inductive coil 316 in series with a second driver inductive coil 318 that collectively act as a differential active coil arrangement. First and second driver inductive coils 316 and 318 are in close proximity with a sense inductive coil 314 which is operatively associated with an differential amplifier 322. In configuration, safety interlock system 311 is arranged such that metallic component 21 is placed adjacent to driver inductive coil 318. The sense inductive coil 314 is located between the first and second driver inductive coils 316 and 318. When no metallic component 21 is present, there is only a small voltage, Vr, produced at the output of differential amplifier 322. However, in the presence of the metallic component 21 within recess 29 the inductance of second driver inductive coil 318 is decreased relative to first driver inductive coil 316 which unbalances the system 311 and causes the voltage at the output of amplifier 322 to increase. This unbalancing of safety interlock system 311 is sensed at Vr, the response voltage of sense coil 314, which is then communicated to microcontroller 40.

It is contemplated that the safety interlock system 11 can be used with different types of flow control apparatuses 12. For example, flow control apparatuses 12 such as peristaltic, linear peristaltic and rotary peristaltic pumps are felt to fall within the present invention. Further, the fluid administration set 14 can have a drip chamber for providing a visual indication of fluid flow, or an ultrasonic sensor arrangement, such as a piezoelectric transmitter and receiver, may be attached to the flow control apparatus 12 in order to detect fluid flow in lieu of a drip chamber.

Although particular embodiments of the invention have been shown, it is not intended that the invention be limited thereby, instead, it is intended that the present invention be limited by only the appended claims.

What claimed is:

1. An enteral feeding system (10) comprising:
   an administration feeding set (14) forming a conduit (23) adapted for fluid flow communication therethrough, the administration feeding set (14) including a magnetically-susceptible, non-magnetic metallic component (21); and
   a flow control apparatus (12) operatively associated with said administration feeding set (14) for establishing fluid flow through said conduit (23), said flow control apparatus (12) further including a sensor arrangement (33) comprising a back-biased sensor (34) and magnet (36), said sensor arrangement (33) generating a magnetic flux for sensing the presence of said component (21) properly received on the flow control apparatus (12), wherein said component (21) changes the magnetic flux and said change in magnetic flux is detectable by said sensor (34) when said administration feeding set (14) is properly engaged to said flow control apparatus (12).

2. The enteral feeding system (10) according to claim 1, wherein said flow control apparatus (12) further includes a recess (29) for receiving the component (21).

3. The enteral feeding system (10) according to claim 2 wherein said sensor (34) detects the presence of the component (21) only when the component (21) is properly seated within the recess (29).

4. The enteral feeding system (10) according to claim 3, wherein said administration feeding set (14) further includes a mounting member (30) for mounting said component (21) in said recess (29).

5. The enteral feeding system (10) according to claim 1, wherein said sensor arrangement (33) is operatively associated with a microcontroller (40), said microcontroller (40) permitting operation of said flow control apparatus (12) when said administration feeding set (14) is properly engaged to said flew control apparatus (12) and prevents operation thereof when said administration feeding set (14) in improperly engaged to said flow control apparatus (12).

6. The enteral feeding system (10) according to claim 1, wherein said component (21) is made of a ferrous alloy.

* * * * *